United States Patent

Lhenry

[11] Patent Number: 5,470,547
[45] Date of Patent: Nov. 28, 1995

[54] DEVICE FOR STERILIZING PRODUCTS AT HIGH PRESSURE

[75] Inventor: Bernard Lhenry, Le Creusot, France

[73] Assignee: Framatome, Courbevoie, France

[21] Appl. No.: 238,867

[22] Filed: May 6, 1994

[30] Foreign Application Priority Data

May 7, 1993 [FR] France .................... 93 05526

[51] Int. Cl.$^6$ .................... A61L 2/00
[52] U.S. Cl. .................... 422/295; 422/292
[58] Field of Search .................... 422/33, 292, 294, 422/295, 296; 99/452, 460, 461

[56] References Cited

U.S. PATENT DOCUMENTS

| 4,552,720 | 11/1985 | Baker, Sr. et al. | 422/294 X |
| 4,667,699 | 5/1987 | Loliger | 138/91 |
| 4,944,923 | 7/1990 | Heinrichs et al. | 422/295 X |
| 4,957,706 | 9/1990 | Romette et al. | 422/102 X |
| 5,286,448 | 2/1994 | Childers | 422/33 X |

FOREIGN PATENT DOCUMENTS

| 480422 | 4/1992 | European Pat. Off. . | |
| 2442018 | 6/1980 | France . | |
| 0565707 | 7/1977 | U.S.S.R. | 422/295 |

OTHER PUBLICATIONS

French Search Report FR 93 05526, Jan. 1994.

Primary Examiner—Robert J. Warden
Assistant Examiner—Robert Carpenter
Attorney, Agent, or Firm—Pollock, Vande Sande & Priddy

[57] ABSTRACT

The high pressure sterilization device comprises a sealed vessel (1) including a bottom wall (10) provided with an opening (12) connected to a source of pressurized fluid and a cover (20) attached to the bottom wall (10), and a slidable piston (30) mounted in a sealed manner in the vessel (1) and adapted to move in the vessel (1) under the effect of the pressure exerted by the fluid on an active surface (31) of the slidable piston (30). A high pressure treatment chamber (5) provided in the slidable piston (30) is adapted to receive the product to be sterilized, and a fixed piston (40) connected to the cover (20) is adapted to penetrate the high pressure treatment chamber (5) when moving the slidable piston (30) so as to compress the product to be sterilized.

11 Claims, 1 Drawing Sheet

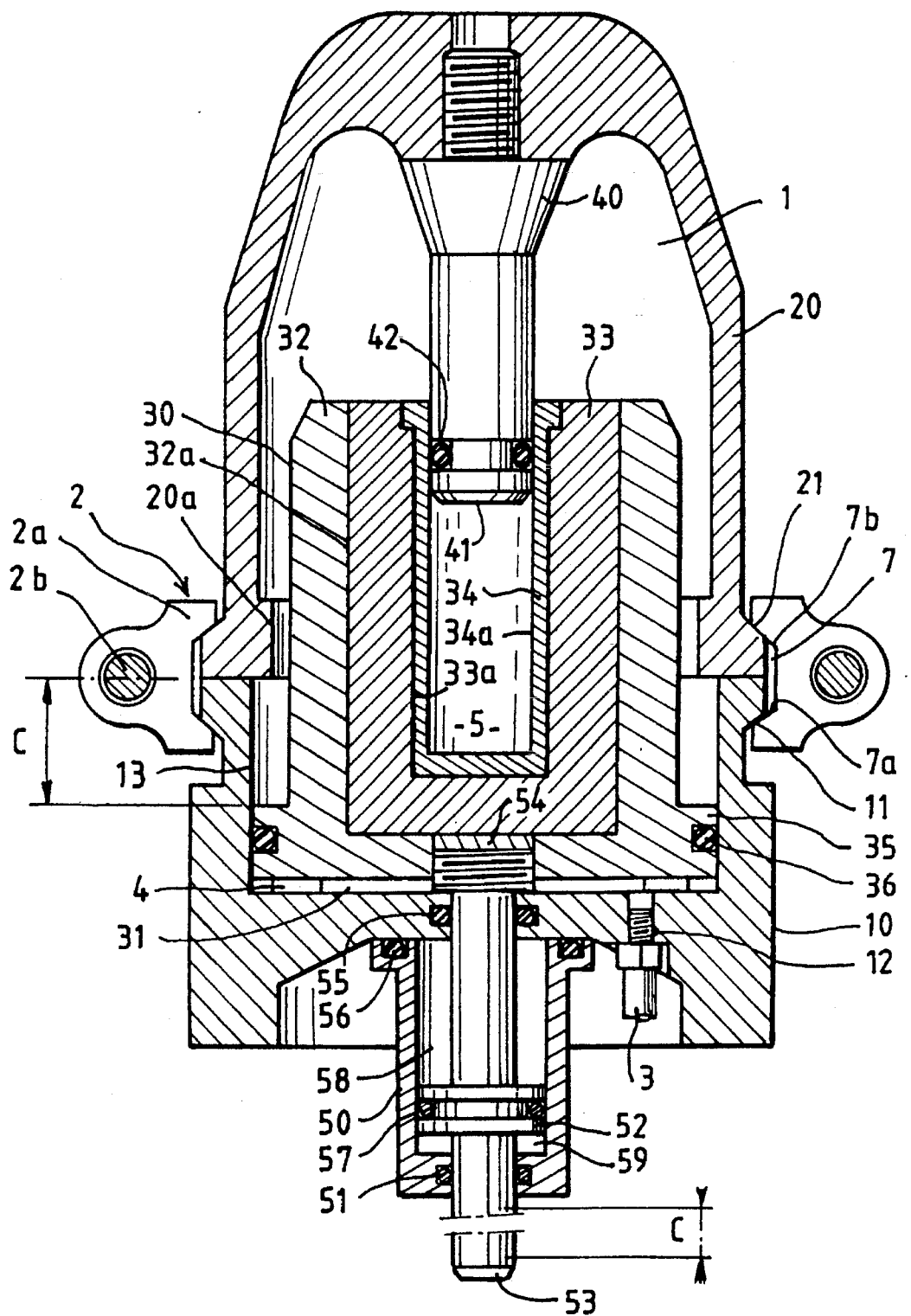

DEVICE FOR STERILIZING PRODUCTS AT HIGH PRESSURE

FIELD OF THE INVENTION

The present invention relates to a device for sterilizing products, such as for example fluids or packaged at high pressure, and is intended more particularly for laboratories.

BACKGROUND OF THE INVENTION

It is known to submit products to be sterilized to a pressure which may reach 8,000 bars.

For this purpose, the products to be sterilized are generally placed into a sealed vessel of small volume and subjected to pressure. The sealed vessel is connected to a pump adapted to pump fluid into the interior of the vessel so as to increase the internal pressure.

In the case of sterilizing a fluid, the latter is contained in the sealed vessel and subjected directly to the desired pressure obtained by means of the pump.

In the case of sterilizing a packaged element, the latter is placed in the sealed vessel and subjected to the required pressure by means of the pump.

Given the high pressure within the sealed vessel necessary to sterilize products, the vessel and the entire sterilization device must be capable of withstanding the high pressures and be safe for the personnel.

The sterilization device must therefore be designed to be entirely, and to avoid failures of the parts subjected to the pressure and, even in the case where such failures occur, it must avoid the serious consequences that this would involve for the surrounding personnel.

SUMMARY OF THE INVENTION

An object of the invention is therefore to propose a device which permits sterilizing products at very high pressure and has all the guarantees of safety expected from this type of device.

The invention therefore provides a device for sterilizing products at high pressure, of the type comprising a sealed vessel including a bottom wall provided with an opening connected to means for feeding fluid under pressure, a cover assembled with the bottom wall by fixing means, and a slidable piston mounted in a sealed manner in the vessel and movable in the vessel under the effect of the pressure exerted by the fluid on an active surface of said slidable piston. The device comprises a high pressure treatment chamber provided in the slidable piston and adapted to receive the product to be sterilized, and a fixed piston connected to the cover and adapted to penetrate the high pressure treatment chamber when the slidable piston is moved for the purpose of compressing said product to be sterilized, the free end of the fixed piston defining an active surface, the ratio between the active surfaces of the slidable piston and fixed piston being 1:20.

According to other features of the invention:

the slidable piston comprises at least two sleeves and concentric and interconnected with a protective inner sheath sleeves, the slidable piston comprises an outer sleeve, an intermediate sleeve and a protective inner sheath, the sleeves and inner sheath being concentric and interconnected, the outer sleeve comprises a blind bore in which the intermediate sleeve is mounted, the intermediate sleeve is mounted in the outer sleeve by a hooping effect or a tight fit, the intermediate sleeve comprises a blind bore concentric with the blind bore of the outer sleeve and in which the inner sheath is mounted, the inner sheath comprises a blind bore which forms the high pressure treatment chamber and is concentric with the blind bores of the outer sleeve and intermediate sleeve, the outer sleeve comprises on the outer surface thereof a sealing element cooperating with the inner surface of the inner sleeve to provide a seal between, a chamber defined by the active surface of the slidable piston and the bottom wall, and the vessel, and the fixed piston comprises on its outer surface a sealing element cooperating with the inner surface of the inner sheath to provided the seal between the high pressure treatment chamber and the vessel.

According to another feature of the invention, the device comprises a cylinder device for returning the slidable piston and comprising a rod extending through the bottom wall in a sealed manner, the rod being connected to the outer sleeve of the slidable piston.

BRIEF DESCRIPTION OF THE DRAWINGS

A better understanding of the invention will be had from the following description which is given solely by way of an example with reference to the accompanying single drawing FIGURE which represents, in section, a high pressure sterilization device according to the invention.

DETAILED DESCRIPTION

The sterilization device shown in section in the drawing comprises a sealed vessel 1 defined by a bottom wall 10 and a cover 20.

The bottom wall 10 and the cover 20 are assembled by fixing means 2 comprising a clamping ring 2a which is either articulated or composed of two semi-rings interconnected by a set of belts 2b.

The clamping ring 2a comprises an inner V-section recess 7 whose first inclined surface 7a bears against an inclined surface 11 provided on the outer surface of the upper portion of the bottom wall 10 and whose second inclined surface 7b bears against an inclined surface 21 provided on the outer surface of the lower portion of the cover 20.

The bottom wall 10 is also provided with an opening 12 connected to means (not shown) for feeding fluid under pressure via a pipe 3.

The bottom wall 10 defines a bore 13 having a flat bottom and in which a slidable piston 30 is mounted.

The lower surface of the piston 30 and the lower surface of the bore 13 of the bottom wall 10 defines an inner chamber 4 which is connected to the means feeding fluid under pressure via the pipe 3.

Thus the slidable piston 30 is adapted to slide in the vessel 1 under the effect of the pressure exerted by the fluid under pressure on the lower surface of the piston 30 which constitutes an active surface 31 of the slidable piston 30.

The slidable piston 30 comprises at least two sleeves 32 and 33 and an inner protective sheath 34, the sleeves 32 and 33 and the inner sheath 34 being concentric and interconnected.

In the embodiment shown, the slidable piston 30 comprises an outer sleeve 32, an intermediate sleeve 33 and a protective inner sheath 34.

For the purpose of guiding the slidable piston 30 as it moves in the bore 13 of the bottom wall 10, the outer sleeve 32 comprises in its lower part a flange 35 which constitutes a stop.

Further, the cover 20 comprises, at the level of its lower end bearing against the bottom wall 10, an inwardly projecting portion 20a adapted to cooperate with the flange 35 for limiting the travel of the slidable piston 30.

The outer sleeve 32 comprises on its outer surface at the level of the flange 35, a sealing element 36 adapted to cooperate with the inner surface of the bore 13 in the bottom wall 10 for providing a seal between the chamber 4 and the vessel 1.

The outer sleeve 32 defines a blind bore 32a in which the intermediate sleeve 33 is mounted, for example by a hooping effect or a tight fit, so that the intermediate sleeve 33 cannot be removed from the outer sleeve 32.

The intermediate sleeve 33 defines a blind bore 33a concentric with the blind bore 32a of the outer sleeve 32 and in which the inner sheath 34 is mounted.

The inner sheath 34 defines a blind bore 34a forming a high pressure treatment chamber 5 concentric with the blind bores 32a and 33a of the outer sleeve 32 and intermediate sleeve 33.

The assembly between the inner sheath 34 and the intermediate sleeve 33 is achieved with relatively narrow tolerances and the purpose of inner sheath 34 is to prevent corrosion under stress of the sleeves 32 and 33.

The type of material employed for the inner sheath 34 is compatible with the product to be sterilized which is disposed in the high pressure treatment chamber, as will be explained hereinafter.

The sterilization device further comprises a fixed piston 40 connected to the cover 20 and disposed on the axis of the slidable piston 30, i.e., on the axis of the high pressure treatment chamber 5.

The fixed piston 40 is adapted to penetrate the high pressure treatment chamber 5 upon the displacement of the slidable piston 30.

The free end of the fixed piston 40 defines an active surface 41.

The ratio between the active surface 31 of the slidable piston 30 and the active surface 41 of the fixed piston 40 is 1:20.

The fixed piston 40 includes on its outer surface a sealing element 42 adapted to cooperate with the inner surface of the inner sheath 34 to provided a seal between the high pressure treatment chamber 5 and the vessel 1.

The sterilization device comprises a cylinder device 50 for returning the slidable piston 30.

The cylinder device 50 comprises in the known manner a body 51 fixed to the exterior of the bottom wall 10, a piston 52 movable in the body 51 and a rod 53 connected to the piston 52 and disposed on the axis of the slidable piston 30.

The rod 53 extends in a sealed manner through the bottom wall 10 and is connected, for example by screwing, to the outer sleeve 32 of the slidable piston 30.

A sealing element 54 is interposed between the end of the rod 53 and the intermediate sleeve 33 of the slidable piston 30.

Further, sealing elements 55, 56 and 57, respectively are interposed between the rod 53 and the bottom wall 10, the body 51 and the bottom wall 10 and the piston 52 and the body 51 of the cylinder device 50.

The piston 52 of the cylinder device 50 delimits with the body 51 of the cylinder device 50 two chambers, 58 and 59, connected to means (not shown) for feeding and aspirating a fluid under pressure, whereby it is possible to return the slidable piston 30 to its initial position by means of piston 52 and the rod 53.

If the product to be sterilized is a fluid, this fluid is placed in the high pressure treatment chamber 5 while, if the product to be sterilized is a packaged element, this packaged element is placed in a fluid contained in the high pressure treatment chamber 5.

The rod 53 of the cylinder device 50 may be connected to electrical or mechanical indicating means indicating the position of the slidable piston 30 in the vessel 1.

The sterilization device according to the invention operates in the following manner:

The fluid entering the chamber 4 by way of the pipe 3 acts on the active surface 31 of the slidable piston 30 and thereby displacing the slidable piston 30 upwardly by distance C.

This distance C is detected by the means for indicating the displacement of the rod 53 of the cylinder device 50, which moves at the same time as the slidable piston 30.

In the course of its displacement, the slidable piston 30 is guided by the flange 35 which cooperates with the bore 13 of the bottom wall 10, and the travel of the slidable piston 30 is limited by this flange 35 and the inwardly projecting portion 20a of the cover 20.

The displacement of the slidable piston 30 in the vessel 1 has the effect of compressing, in cooperation with the fixed piston 40, the product contained in the high pressure treatment chamber 5 and of sterilizing this product.

The maximum pressure in the treatment chamber 5 may reach 8,000 bars, and this pressure is exerted, either directly on the product to be sterilized in the case of a fluid, or through the medium of the liquid contained in the treatment chamber 5 in the case of a packaged element plunged into the liquid.

The maximum pressure of 8,000 bars may be reached owing to the ratio between the active surface 31 of the slidable piston 30 and the active surface 41 of the fixed piston 40 which is 1:20.

The sterilization device according to the invention has the advantage of being composed of a minimum number of parts, thereby limiting the interfaces subjected to the maximum pressure of 8,000 bars.

Indeed, the high pressure treatment chamber 5 is delimited by a slidable piston 30 composed of at least three concentric parts and by a fixed piston 40 performing the function of a plug for high pressure treatment chamber 5.

The third element subjected to the high pressure is the sealing element 42 mounted on the end portion of the fixed piston 40.

The sterilization device according to the invention therefore comprises only three elements directly subjected to the maximum pressure.

The high pressure is therefore confined in the treatment chamber 5.

A possible failure of the sealing element 42 may result in leakages which normally are particularly dangerous but which, in the device according to the invention, are strictly confined in the internal volume defined by the bottom wall 10 and the cover 20.

A possible crack in the bottom wall 10 or in the cover 20 has no serious consequence, since the pressure within the vessel 1 is very low relative to the mechanical resistance of the bottom wall 10 and the cover 20.

The assembly of the bottom wall 10 and the cover 20, which may be taken down, is not put under great stress owing to its dimensions, which correspond to the design of a 400-bar cylinder device.

The sterilization device according to the invention therefore has the advantage of bringing the conditions of use of a very high pressure device to surrounding levels of stresses corresponding to devices operating under conventional pressure.

The sterilization device according to the invention therefore has all the safety guarantees essential in the use of a very high pressure.

What is claimed is:

1. Device for the sterilization of a product at high pressure, comprising, in combination,
   (a) a sealed vessel including a bottom wall having an opening for connection to means for feeding fluid under pressure;
   (b) a cover;
   (c) a fixing means for assembling and fixing said cover to said bottom wall;
   (d) a slidable piston having a first active surface on a bottom wall of said slidable piston, and adjacent said bottom wall, said slidable piston being mounted in a sealed manner in said vessel to be slidable in said vessel under the effect of pressure exerted by said fluid on said active surface of said slidable piston;
   (e) a sterilization pressure treatment chamber provided in said slidable piston for receiving a product to be sterilized; and
   (f) a fixed piston connected to said cover and adapted to penetrate said sterilization pressure treatment chamber when said slidable piston is moved for the purpose of compressing said product to be sterilized, said fixed piston having a free end defining a second active surface, a ratio between areas of said first and second active surfaces being approximately 1:20;
   (g) wherein said slidable piston comprises at least two sleeves and a protective inner sheath, said at least two sleeves and said inner sheath being concentric and interconnected.

2. Device according to claim 1, wherein said slidable piston comprises an outer sleeve, an intermediate sleeve and a protective inner sheath, said outer sleeve, said intermediate sleeve and said inner sheath being concentric and interconnected.

3. Device according to claim 2, wherein said outer sleeve comprises a blind bore in which said intermediate sleeve is mounted.

4. Device according to claim 3, wherein said intermediate sleeve is mounted in said outer sleeve by a fit sufficiently tight to prevent removal of said intermediate sleeve from said outer sleeve.

5. Device according to claim 3, wherein said intermediate sleeve comprises a blind bore concentric with said blind bore of said outer sleeve and in which said inner sheath is mounted.

6. Device according to claim 3, wherein said intermediate sleeve comprises a blind bore, and said inner sheath comprises a blind bore which constitutes said pressure treatment chamber and is concentric with said blind bores of said outer sleeve and intermediate sleeve.

7. Device according to claim 2, wherein a second chamber is defined between said active surface of said slidable piston and said bottom wall, said outer sleeve has an outer surface, said inner sleeve has an inner surface, said outer sleeve comprises on said outer surface thereof a sealing element cooperative with said inner surface of said inner sleeve for providing a seal between said second chamber and said vessel.

8. Device according to claim 1, wherein said fixed piston has an outer surface, said inner sheath has an inner surface, said fixed piston comprising on said outer surface thereof a sealing element cooperative with said inner surface of said inner sheath for providing a seal between said high pressure treatment chamber and said vessel.

9. Device according to claim 1, comprising a cylinder device cooperating with said slidable piston for returning said slidable piston.

10. Device according to claim 9, wherein said cylinder device comprises a rod extending in a sealed manner through said bottom wall and connected to said outer sleeve of said slidable piston.

11. Device according to claim 10, further comprising means for indicating the position of said slidable piston in said vessel and connected to said rod of said cylinder device.

* * * * *